(12) United States Patent
Yoon et al.

(10) Patent No.: US 11,000,479 B2
(45) Date of Patent: May 11, 2021

(54) INJECTABLE LONG-ACTING NALTREXONE MICROPARTICLE COMPOSITIONS

(71) Applicants: Chong Kun Dang Pharmaceutical Corp., Seoul (KR); Purdue Research Foundation, West Lafayette, IN (US)

(72) Inventors: Gwangheum Yoon, West Lafayette, IN (US); Bong Kwan Soh, West Lafayette, IN (US); Andrew David Otte, West Lafayette, IN (US); Kinam Park, West Lafayette, IN (US)

(73) Assignees: Chong Kun Dang Pharmaceutical Corp., Seoul (KR); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/653,707

(22) Filed: Oct. 15, 2019

(65) Prior Publication Data

US 2020/0113835 A1 Apr. 16, 2020

Related U.S. Application Data

(60) Provisional application No. 62/745,805, filed on Oct. 15, 2018.

(51) Int. Cl.
*A61K 9/16* (2006.01)
*A61K 9/00* (2006.01)
*A61K 31/485* (2006.01)

(52) U.S. Cl.
CPC .......... *A61K 9/1647* (2013.01); *A61K 9/0019* (2013.01); *A61K 9/1611* (2013.01);
(Continued)

(58) Field of Classification Search
CPC .. A61K 9/1647; A61K 9/0019; A61K 9/1694; A61K 9/1652; A61K 9/1623;
(Continued)

(56) References Cited

U.S. PATENT DOCUMENTS 6,306,425 B1 10/2001 Tice et al.
7,157,102 B1 1/2007 Nuwayser
(Continued)

FOREIGN PATENT DOCUMENTS

CN 1415294 5/2003
EP 1786400 B1 3/2009
(Continued)

OTHER PUBLICATIONS

Dinarvand et al. Preparation of Biodegradable Microspheres and Matrix Devices Containing Naltrexone, AAPS PharmSciTech, 4(3), Article 34, pp. 1-10 (Year: 2003).*
(Continued)

*Primary Examiner* — Carlos A Azpuru
(74) *Attorney, Agent, or Firm* — Fish & Richardson P.C.

(57) ABSTRACT

The present disclosure relates to naltrexone sustained release microparticle delivery systems for the treatment of diseases ameliorated by naltrexone. The injectable microparticle delivery system includes naltrexone encapsulated in biodegradable microparticles administered in a pharmaceutically acceptable vehicle.

17 Claims, 5 Drawing Sheets

(52) U.S. Cl.
CPC .......... *A61K 9/1623* (2013.01); *A61K 9/1652* (2013.01); *A61K 9/1664* (2013.01); *A61K 9/1694* (2013.01); *A61K 31/485* (2013.01)

(58) Field of Classification Search
CPC .. A61K 9/1664; A61K 9/1611; A61K 9/5153; A61K 31/485
See application file for complete search history.

(56) References Cited

U.S. PATENT DOCUMENTS

| | | |
|---|---|---|
| 7,279,579 B2 | 10/2007 | Brittain et al. |
| 7,799,345 B2 | 9/2010 | Zale et al. |
| 7,914,804 B2 | 3/2011 | O'Neil et al. |
| 7,919,499 B2 | 4/2011 | Ehrich |
| 8,343,528 B2 | 1/2013 | Kuo et al. |
| 2015/0265535 A1 | 9/2015 | Yu et al. |

FOREIGN PATENT DOCUMENTS

| | | |
|---|---|---|
| WO | WO 2009/058147 | 5/2009 |
| WO | WO 2017/033208 | 3/2017 |

OTHER PUBLICATIONS

Makadia et al, Poly Lactic-co-Glycolic Acid (PLGA) as Biodegradable Controlled Drug Delivery Carrier, Polymers, Sep. 1, 3(3), 1377-1397. (Year: 2011).*

PCT International Search Report and Written Opinion in International Appln. No. PCT/KR2019/013535, dated Jan. 29, 2020, 13 pages.

Andhariya et al., Accelerated In Vitro Release Testing Method of Naltrexone Loaded PLGA Microspheres, Int. J. Pharm. 520 (1-2): 79-85, 2017.

Brewer, Colin, Serum Naltrexone and 6-beta-Naltrexol Levels from Naltrexone Implants Can Block Very Large Amounts of Heroin: A Report of Two Cases. Addict. Biol., 7:321-323, 2002.

Comer, Sandra D., Depot naltrexone: Long-lasting antagonism of the effects of heroin in humans. Psychopharmacology, 159:351-360, 2002.

Dean, Reginald L., The Preclinical Development of Medisorb Naltrexone, a Once a Month Long-Acting Injection for the Treatment of Alcohol Dependence, Frontiers in Bioscience 10: 643-655, 2005.

Garbutt et al., Efficacy and Tolerability of Long-Acting Injectable Naltrexone for Alcohol Dependence: A Randomized Controlled Trial, JAMA. 293(13):1617-1625, 2005.

Hulse et al., Reducing hospital presentations for opioid overdose in patients treated with sustained release naltrexone implants. Drug Alcohol Depend., 79:351-357, 2005.

Hulse, Improving Clinical Outcomes for Naltrexone as a Management of Problem Alcohol Use. Br. J. Clin. Pharmacol. 76(5) 632-641, 2013.

Johnson et al., A pilot evaluation of the safety and tolerability of repeat dose administration of long-acting injectable naltrexone (Vivitrex) in patients with alcohol dependence, Alcohol Clin Exp Res. 28(9):1356-61, 2004.

Toljan and Vroman, Low-dose Naltrexone (LDN)—Review of Therapeutic Utilization, Med Sci. 6:82, 2018.

Verebey et al., Naltrexone: Disposition, Metabolism, and Effects After Acute and Chronic Dosing. Clin. Pharmacol. Ther., 20:315-328, 1976.

Chemistry Review Application 21-897, Apr. 7, 2006 (35 pages).

Naltrexone Pharmacokinetics, https://en.wikipedia.org/wiki/Naltrexone, Nov. 12, 2020 (9 pages).

* cited by examiner

INJECTABLE LONG-ACTING NALTREXONE MICROPARTICLE COMPOSITIONS

RELATED APPLICATIONS

This application claims priority under 35 U.S.C. § 119(e) to U.S. Application No. 62/745,805 filed Oct. 15, 2018, which application is incorporated herein by reference.

STATEMENT OF FEDERALLY SPONSORED RESEARCH

This invention was made with government support under Grant no. 1UG3DA048774-01, awarded by the National Institutes of Health. The government has certain rights in the invention.

FIELD OF THE INVENTION

The present disclosure relates to naltrexone sustained release microparticle delivery systems for the treatment of diseases ameliorated by naltrexone. The injectable microparticle delivery system includes naltrexone encapsulated in biodegradable microparticles administered in a pharmaceutically acceptable vehicle.

BACKGROUND OF THE INVENTION

Substance abuse is a disease that remains prevalent throughout society. Typically thought of as an inner-city issue as it was during the heroin epidemic of the 1960s and 1970s, the issue of opioid abuse has become more prevalent throughout the country, spreading from inner cities to rural communities. The number of substance abusers has risen dramatically in the last few decades, specifically with regards to opioid-based drugs, both pharmaceutical formulations and illicit street drugs.

While oral daily administration of naltrexone is effective, its major problem is very low compliance or noncompliance. The requirement of monthly administration was shown to have high attrition rates (25-36%) post 60 days of treatment initiation [Garbutt et al., *Efficacy and tolerability of long-acting injectable naltrexone for alcohol dependence; a randomized controlled trial*. JAMA. 293(13): 1617-1625, 2005; Hulse *Improving clinical outcomes for naltrexone as a management of problem alcohol use*. Br. J. Clin. Pharmacol. 76(5) 632-641, 2013.] Thus, a longer acting naltrexone formulation is expected to improve patient compliance, reduce relapse, and yield more stable patient outcomes over time.

Various slow release naltrexone loaded microparticles have been characterized. Ehrich (U.S. Pat. No. 7,919,499, *Naltrexone long acting formulation and methods of use*) and Brittain et al. (U.S. Pat. No. 7,279,579 B2, *Polymorphic forms of naltrexone*) teach long-acting formulations of naltrexone in poly(lactide-co-glycolide) (PLGA) comprising about 310 mg to about 480 mg releasing naltrexone for a period of about four weeks. Tice et al. (U.S. Pat. No. 6,306,425 B1, *Injectable naltrexone microsphere compositions and their use in reducing consumption of heroin and alcohol*) teach injectable slow release naltrexone formulations in a poly(D,L-lactide) (PDLL) matrix releasing about 10-40% per week of the initial naltrexone amount over a 4-week period. Nuwayser (U.S. Pat. No. 7,157,102 B1, *Multi-layered microcapsules and method of preparing same*) teaches multi-layered multicapsules with high naltrexone loading (>40% w/w) for one-month delivery. All of the disclosed naltrexone-based microparticle formulations have shown maximum release profiles of about 4 weeks, or a month. Thus, there is a need in the art to prepare long-acting microparticle formulations for delivery greater than 4 weeks or a month.

Slow release naltrexone implant-based long-acting delivery systems have been developed that deliver greater than 4 weeks, or one month. Kuo and Kuzma (U.S. Pat. No. 8,343,528, Long term drug delivery devices with polyurethane based polymers and their manufacture), Saxena and Saxena (WO/2017/033208, Implantable naltrexone tablets), and O'Neil and Liu (U.S. Pat. No. 7,914,804, Slow release pharmaceutical preparation and method of administering the same) all disclose long-acting naltrexone implant-based delivery systems. These implant-based formulations typically require an outpatient surgical procedure to place the implant. While these systems may demonstrate longer release profiles than microparticle-based formulations of naltrexone in some instances, the required surgical procedure and risks of patient self-removal can outweigh the benefits.

Vivitrol® (Alkermes, Inc.) is currently prescribed for the prevention of relapse to opioid dependence following opioid detoxification of about 7-10 days. The recommended dose is 380 mg delivered intramuscularly every 4 weeks or once a month. The injection consists of polymer microparticles suspended in a diluent (an aqueous vehicle) injected with a 20 gauge (G) needle. The 20 G needle is required due to the injection being intramuscularly in the gluteal region, the quantity of microparticles and diluent, and finally the microparticle size and size distribution. The microparticles have been reported to have a $d_{50,volume}$ of 108.49 μm and $d_{50,population}$ of 58.46 μm (Andhariya et al., *Accelerated in vitro release testing method of naltrexone loaded PLGA microspheres* Int. J. Pharm. 520 (1-2) 79-85, 2017), where $d_{50,volume}$ is where 50% of the particles by volume have a diameter greater than 108.49 μm and 50% of the particles by volume have a diameter less than 108.49 μm. A $d_{50,population}$ value of 58.46 indicates that 50% of the particles by number have a diameter greater than 58.46 μm and 50% of the particles by number have a diameter less than 58.46 μm. Thus, there is a need in the state of the art to prepare naltrexone loaded microparticles with smaller microparticle sizes in an effort to provide patients with a lower needle diameter, or higher gauge needle, for administration purposes.

Serum naltrexone levels of 2.8 ng/mL were shown to be sufficient to block doses of pure diamorphine as high as 500 mg in two patients (C. Brewer. *Serum naltrexone and 6-beta-naltrexol levels from naltrexone implants can block very large amounts of heroin: a report of two cases*. Addict. Biol., 7:321-323, 2002), 2.4 ng/mL completely antagonized 25 mg of heroin (Verebey et al., *Naltrexone: Disposition, metabolism, and effects after acute and chronic dosing*. Clin. Pharmacol. Ther., 20:315-328, 1976), and levels of 1-2 ng/mL have been targeted as being sufficient to offer protection from fatal opioid overdose (Hulse et al., *Reducing hospital presentations for opioid overdose in patients treated with sustained release naltrexone implants*. Drug Alcohol Depend., 79:351-357, 2005 and Comer et al. *Depot naltrexone: Long-lasting antagonism of the effects of heroin in humans*. Psychopharmacology, 159:351-360, 2002). In a pilot Vivitrex® study, prior to the second injection, the mean trough plasma naltrexone concentration was 1.23 ng/ml (±0.83 ng/ml), and this remained relatively constant for the remainder of the study; the average mean trough naltrexone level was 1.33 ng/ml (±1.74 ng/ml) (Johnson et al., *A pilot* evaluation of the safety and tolerability of repeat dose administration of long-acting injectable naltrexone (Vivitrex®) in patients with alcohol dependence. Alcohol Clin Exp Res. 28:1356-1361, 2004). In the rat model, a plasma naltrexone concentration of ~1-2 ng/mL was shown to be effective in a "morphine induced analgesia hot-plate test" (*The preclinical development of Medisorb Naltrexone, a once a month long-acting injection for the treatment of alcohol dependence*. Frontiers in Bioscience 10: 643-655, 2005). Thus, there is need in the state of the art to provide rapid therapeutic levels of naltrexone, with a minimal initial burst release, with a minimized maximum concentration thereby providing more stable therapeutic naltrexone levels, for longer than one month, and as a dosage form in an injectable format.

Lower naltrexone doses, termed low dose naltrexone (LDN) (1 to 5 mg oral daily), very low-dose naltrexone (VLDN) (1 µg to 1 mg), and ultra-low-dose naltrexone (ULDN) (less than 1 µg) have shown different pharmacodynamic responses than the classically prescribed dose of 50 mg daily oral (Toljan and Vrooman, *Low-dose naltrexone (LDN)—Review of therapeutic utilization*, Med Sci. 6, 82, 2018). LDN acts as a glial modulator, providing potential benefits to conditions such as fibromyalgia, Crohn's disease, multiple sclerosis, complex-regional pain syndrome, and cancer. ULDN mechanism appears to be related to a bimodal cellular response to opioids, where it has been used in postoperative control of analgesia, reducing the total quantity of opioids. Thus, there is a need in the state of the art to provide stable therapeutic concentrations of low dose naltrexone levels (such as LDN, VLDN, ULDN, etc.).

Many constraints are imposed on formulations having desirable properties: the release of drug must occur over an extended period of time, the loading of drug must be sufficient, the polymeric matrix must be biodegradable and biocompatible, residual chemicals and solvents should be below the maximum acceptable level, and the microspheres must be small enough and capable of passing through patient friendly needles, among others. The physicochemical properties of the microparticles are sensitive to the properties of the drug, polymeric matrix properties, the properties of release modifiers, as well as the processing steps that the microparticles are prepared under.

A variety of methods have been disclosed on how to encapsulate compounds in the form of microparticles. In these methods, the drug or other active compounds are generally dissolved, dispersed, or emulsified using stirrers, homogenizers, or other dynamic mixing elements in a solvent, usually an organic solvent, to form a solution containing the matrix material. Organic solvent is then removed from the drug-matrix material during extraction and/or additional washing steps and the microparticle product is obtained thereafter. Many parameters used in the microparticle preparation affect the properties of the obtained microparticles.

There is a need in the art for a method of preparing microparticles that can release naltrexone longer than one month. The present disclosure, the description of which is fully described below, solves the need for formulations providing naltrexone release for longer than one month.

SUMMARY OF THE INVENTION

The present disclosure relates to injectable, controlled-release (or sustained-release) naltrexone microparticle formulations comprising naltrexone and a biodegradable polymer such as poly(lactide-co-glycolide), also known as poly (lactic-co-glycolic acid) (PLGA), for longer than one month. The microparticles (microspheres) can be readily injected subcutaneously or intramuscularly. More particularly, the present disclosure relates to a method for preparing injectable microparticles having unique release profiles of naltrexone for longer than 4 weeks, preferably about 8 weeks to about 12 weeks, more preferably up to 100 days. The microparticles are prepared by solvent extraction/evaporation of an oil-in-water emulsion, the dispersed oil phase being solutions formed by using an organic solvent, including mainly of naltrexone and biodegradable, biocompatible polymer.

Embodiments of the disclosure are described in detail, including certain preferred and optional embodiments, so that various aspects of the disclosure thereof may be more fully understood and appreciated. Disclosed herein are injectable naltrexone microparticle formulations which provide controlled release of active agent for longer than 4 weeks, particularly about 8 weeks to about 12 weeks (or 100 days).

Long-acting formulations may be prepared through spray drying, emulsion-based techniques, extrusion, microfabrication-based techniques, coacervation, and other processes to manufacture drug-polymer microparticles that possess controlled release properties.

In one embodiment, a method is provided for forming microparticles for use as a controlled release delivery system. The method for preparing an injectable microparticle formulation comprises: (a) mixing a first phase comprising poly(vinyl alcohol) (PVA) and a first solvent, and a second phase comprising a biodegradable polymer, naltrexone and a second solvent to prepare a mixture; and (b) performing an extraction process on the mixture with water or an aqueous solution to obtain microparticles. Preferably, the method comprises a drying process on the microparticles after the extraction process. In another embodiment, the method optionally comprises (c) performing a further extraction process on the microparticle with an ethanolic aqueous solution after the (b) performing the extraction process. When the method comprises the further extraction process, the drying process on the microparticles is performed before and/or after the further extraction process. For example, the drying the particles is performed after the (b) performing the extraction process, after the (c) performing the further extraction process, or after each of (b) and (c).

Figure 1:
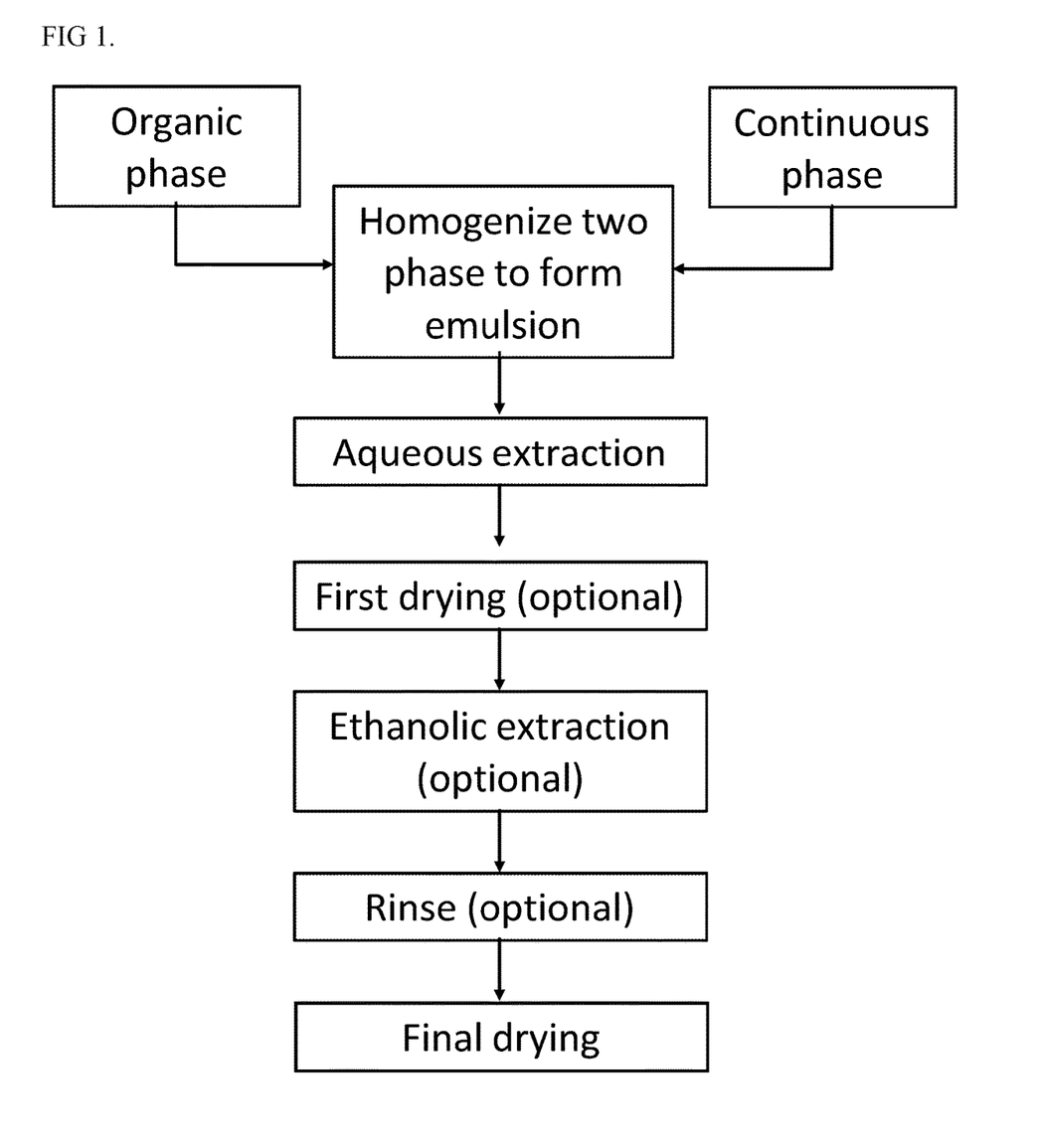
FIG. 1 shows a flow diagram illustrating one embodiment of a method for preparing microparticles.

The methods according to embodiments of the present invention are described in detail with reference to FIG. 1. In the present disclosure, the use of the term "first" or "second" is only intended to explain the present disclosure more conveniently, but these terms do not represent or imply that there is a particular order or degree of importance between them. In addition, a singular form of expression throughout the present disclosure includes a plural meaning as well unless it is contextually clear there is a difference.

The mixing of the first phase and the second phase is performed in any order. In one aspect, but not limited to, the first phase may be added to the top of the second phase and then mixed to prepare the mixture. This process may be emulsification, and the mixture is an oil-in-water emulsion of polymer, naltrexone, and one or more solvents. Oil particles in the mixture (emulsion) become microparticles through a follow-up process of the present disclosure. The mixing may be a process to form microparticles of desired size range, which may depend on the mixing conditions such as rotation speed, power and the like.

The first phase may be also called a continuous phase in the present disclosure. The first phase comprises poly(vinyl alcohol) and the first solvent, wherein the first solvent comprises at least one selected from the group consisting of water, dichloromethane (DCM), benzyl alcohol (BA), and ethyl acetate (EA). In one aspect, the first solvent must comprise water. For example, the first solvent may be water and the first phase may be formed by addition PVA into water.

In another aspect, the first solvent may further comprise an organic solvent, which is at least one selected from the group consisting of dichloromethane, benzyl alcohol, and ethyl acetate. When the first solvent comprises water and one or more organic solvents, the organic solvent could be mixed together with poly(vinyl alcohol) and water when preparing the first phase. In other aspects, when the first solvent comprises water and one or more organic solvents, the organic solvent could be mixed with a solution including poly(vinyl alcohol) and water immediately after mixing poly(vinyl alcohol) and water when preparing the first phase. In another aspect, when the first solvent comprises water and one or more organic solvents, the organic solvent could be mixed with the solution comprising poly(vinyl alcohol) and water immediately before mixing the first phase with the second phase. Preferably, one or more organic solvents may be mixed with a solution comprising poly(vinyl alcohol) and water immediately before mixing with the second phase.

In one aspect, the continuous phase (first phase) comprises about 0.1~5% (w/v) poly(vinyl alcohol) (PVA) in water. In another aspect, the continuous phase may further comprise 0 to 1.8% (w/v) dichloromethane (DCM) and/or 0 to 3.3% (w/v) benzyl alcohol.

The second phase may be also called an organic phase in the present disclosure. The second phase comprises biodegradable polymer, naltrexone and the second solvent, wherein the second solvent comprises at least one selected from the group consisting of dichloromethane, benzyl alcohol, and ethyl acetate. In one aspect, the second solvent comprises dichloromethane and benzyl alcohol, ethyl acetate or a combination thereof. In another aspect, for the preparation of the microparticles, the second phase comprises about 1~40% (w/w) biodegradable polymer dissolved in an organic solvent, such as dichloromethane (DCM), also known as methylene chloride, and 1~50% (w/w) naltrexone dissolved in another organic solvent, such as benzyl alcohol. The naltrexone could be used in the method in the form of free base, salt, solvate, cocrystal or combinations thereof.

The biocompatible, biodegradable polymer may be a homopolymer, copolymer, or terpolymer or repeating monomeric units linked by groups such as ester groups. The polymer may be a polyester that may be composed of units of about one or more hydroxycarboxylic acid residues, where the distribution of units may be random, blocked, paired, or distributed sequentially. When the biodegradable polymer is a polyester, the polyesters include polylactide, polyglycolide, and PLGA. In one aspect, the biodegradable polymer is a polylactide, PLGA, or combinations thereof. Preferably, the suitable biodegradable polyester has the lactide:glycolide (L:G) (molar) ratio of 50:50 to 100:0, preferably 65:35 to 90:10, more preferably 75:25 to 85:15. Preferably, the suitable biodegradable polyester is a 60:40 to 95:5 PLGA. More preferably, the suitable biodegradable polyester is a 70:30 to 90:10 PLGA. Even more preferably, the biodegradable polyester is a 75:25 to 85:15 PLGA. The most preferably, the biodegradable polyester is an 85:15 PLGA. In one aspect, the biodegradable polymer has an average molecular weight of 50,000 to 150,000 Daltons.

The mixture (emulsion) is subjected to an appropriate solvent extraction process to obtain the microparticles, ultimately decreasing the solvent levels to an acceptable level. The terms "extract," "extracting," and "extraction" in the present disclosure refer to bringing the mixture or emulsion comprising poly(vinyl alcohol), the biodegradable polymer, naltrexone, and one or more solvents into contact with an extraction phase. One or more organic solvents are removed from oil particles of the mixture (emulsion) during the solvent extraction process, and the microparticles comprising polymer and naltrexone are consequently obtained.

The solvent extraction process comprises at least one extraction process. The extraction process (first) is performed on the mixture (emulsion) with an extraction phase to obtain the microparticles, wherein the extraction phase is water or an aqueous solution. The aqueous solution may comprise at least one selected from the group consisting of poly(vinyl alcohol), dichloromethane, benzyl alcohol, and ethyl acetate. Preferably, the extraction phase may be water with 0 to 3% (w/v) of at least one selected from the group consisting of polyvinyl alcohol, dichloromethane, benzyl alcohol, and ethyl acetate. More preferably, the extraction phase may be water with 0~2% (w/v) poly(vinyl alcohol), 0~1.8% (w/v) dichloromethane, 0~2% (w/v) benzyl alcohol, or 0~3% (w/v) ethyl acetate.

When the solvent extraction process comprises two extraction processes, the further extraction process (second) may be performed on the microparticles with an ethanolic aqueous solution (It is also called an ethanolic extraction phase or ethanol solution in the present disclosure). The ethanolic extraction phase is an aqueous solution of about 1~50% (v/v) ethanol.

The temperatures of each extraction process may be in the range of about 4~30° C. Preferably, the first (aqueous) extraction process may be performed in the temperature range of about 4 to 10° C. Preferably, the second (ethanolic) extraction process may be performed in the temperature range of about 20 to 30° C. The extraction time may be in the range of about 2 to 8 hours.

In one aspect, after performing the solvent extraction process, drying the microparticles is optionally performed. The drying may be under vacuum in the temperature range of about 4~30° C. or other drying processes such as lyophilization. When the solvent extraction process comprises two extraction processes, a further drying process may be optionally performed between two extraction processes. Intermediate drying may be performed under vacuum in the temperature range of about 4~30° C.

Before each drying process, the method comprises a collecting process for collecting the microparticles from the mixture (emulsion), solution, dispersion, etc. The collecting process is performed with sieves having various pore sizes. The pore sizes of the sieves are in the range of 10-200 µm.

The method also may optionally comprise a rinse process after the solvent extraction process. When the method comprises collecting process, the rinse process may be performed after collecting but before drying. The rinse process may be a process of removing residues such as solvents, unreacted substances, etc., in the present disclosure.

In one embodiment, an injectable microparticle formulation is provided. In one aspect, the injectable microparticle formulation is prepared according to the method of the present invention.

The injectable microparticle formulation of the present disclosure comprises microparticles including naltrexone and the biodegradable polymer. The microparticle has sustained-release profiles of naltrexone. In one aspect, the sustained release of naltrexone is longer than 4 weeks and up to 100 days. In another aspect, the sustained release of naltrexone is about 8 weeks to about 12 weeks. The microparticle comprises about 20-40% (w/w) of naltrexone. The naltrexone may be in the form of free base, salt, solvate, cocrystal or combinations thereof.

The biodegradable polymer comprises a polylactide, poly (lactide-co-glycolide), or combinations thereof. Preferably, the lactide:glycolide (L:G) (molar) ratio of the biodegradable polymer may be 50:50 to 100:0, preferably 65:35 to 90:10, more preferably 75:25 to 85:15. The molecular weight of the biodegradable polymer may be 50,000 Dalton to 150,000 Daltons.

In a preferred embodiment, the injectable naltrexone microparticles comprise naltrexone in an 85:15 PLGA with a molecular weight of at least 50,000 Daltons, such as those described below in the examples. Preferably, the molecular weight of PLGA is 50,000 Dalton to 150,000 Daltons.

In one preferred embodiment, the naltrexone is present in the long acting formulation in the amount of at least about 20% by weight, preferably at least about 30% by weight, more preferably at least about 35% by weight, such as about 40% by weight naltrexone of the total weight of the formulation. In one aspect, the naltrexone is present in the long acting formulation in the amount of about 20-40% (w/w).

The microparticles can be prepared in a size distribution range suitable for subcutaneous and/or intramuscular injection using needles thinner than 20 G. The particle diameter, shape, morphology, and porosity can be manipulated in such a way to control the release characteristics and allow passage through a syringe and needle. The naltrexone loaded microparticles may have a particle size distribution with the range of 1 to 200 μm. More preferably, the particle size distribution may have a range of about 10~125 μm. Even more preferably, the particle size distribution may have a range of about 25~100 μm. In one aspect, the microparticles have an average particle size in the range of 25 to 125 μm.

In one embodiment, a method is provided of injecting the biodegradable microparticles. The method includes injecting a flowable composition including the biodegradable microparticles in an acceptable (biocompatible) vehicle. The acceptable (biocompatible) vehicle includes an aqueous-based vehicle, an oil-based vehicle or combination thereof. Preferably, the acceptable vehicle is an aqueous based system. This aqueous based system comprises a tonicity agent such as sodium chloride, a viscosity enhancing agent such as sodium carboxymethylcellulose, a wetting agent such as polysorbate, or combinations thereof. In one aspect, the aqueous based system may be composed of wetting agents such as polysorbate 20 and viscosity enhancing agents, such as sodium carboxymethylcellulose, hyaluronic acid, and the like. Another acceptable vehicle may be an oil based vehicle that may also act as a water uptake rate limiter and/or diffusion barrier, thus altering the release rate either by limiting the initial release or decreasing the steady state rate. The biocompatible oil vehicle comprises peanut oil, castor oil, sesame oil, sunflower oil, soybean oil, corn oil, cottonseed oil, or any combination thereof. In one aspect, the suitable acceptable vehicle may be a combination of the aqueous based vehicle and the oil based vehicle. The microparticles may be administered subcutaneously or intramuscularly.

In one embodiment, the controlled release formulation provides therapeutically beneficial amounts of naltrexone to the subject for a period of at least 4 weeks, preferably at least 6 weeks, more preferably at least 8 or more weeks.

In one preferred embodiment, the duration of action of naltrexone using the same dose (380 mg of naltrexone) as used in Vivitrol provides therapeutically beneficial amounts of naltrexone for greater than 4 weeks, preferably 6 weeks, more preferably 8 weeks, and even more preferably 12 weeks.

In one embodiment, a method is provided of treating or preventing diseases related to opioid abuse or overdoses, alcohol dependence, or pain by naltrexone or a metabolite. The method includes administering to a patient (subject) in need of such a treatment or prevention an effective amount of the microparticle comprising naltrexone, the microparticle formulation comprising the microparticle, or composition comprising the microparticle or the microparticle formulation.

In another embodiment, a composition comprising the injectable microparticle formulation is provided. The composition may comprise a biocompatible vehicle, wherein the biocompatible vehicle includes the aqueous-based vehicle, the oil-based vehicle, or both. In one aspect, the composition is formulated as injection(s).

In one embodiment, a composition comprising the injectable microparticle formulation for use in treatment or prevention of diseases related to opioid abuse or overdoses, alcohol dependence, or pain is provided. The composition may comprise a biocompatible vehicle, wherein the biocompatible vehicle includes the aqueous-based vehicle, the oil-based vehicle, or both. In one aspect, the composition is formulated as injection(s).

In other embodiments, a use of the injectable microparticle formulation for treating or preventing diseases related to opioid abuse or overdoses, alcohol dependence, or pain is provided.

In another embodiment, a use of the injectable microparticle formulation in preparation of a medicament for treating or preventing diseases related to opioid abuse or overdoses, alcohol dependence, or pain is provided.

The release profile may vary depending upon the L:G ratio, molecular weight, end group, and polydispersity of the biodegradable, biocompatible PLGA polymer, the residual solvent content, manufacturing methodology, among other factors. Second, the release profile may vary between in vitro and in vivo conditions, due to such factors as temperature differences between in vitro and in vivo experiments, release media versus interstitial fluid differences, and/or vehicle used for administration.

By providing microparticles which have releasing capabilities of longer than 4 weeks, in particular, about 8 to 12 weeks (or 100 days), subjects will receive fewer injections and require less visits to physician offices. The microparticles of the present disclosure show an exemplary sustained release of naltrexone both in in vivo and in vitro conditions. To provide for better patient compliance, the size of the microparticles and/or amount of naltrexone may be modified.

DESCRIPTION OF THE DRAWINGS

FIG. 2. illustrates the in vitro release profile (FIG. 2A) and the in vivo pharmacokinetic profiles (FIG. 2B) of formulations from Example 1.

FIG. 4. illustrates the in vivo pharmacokinetic profiles of Formulations 12-3 (FIG. 4A), 12-4 (FIG. 4B), 12-5 (FIG. 4C), and 12-7 (FIG. 4D) of Table 10 in Example 12.

The following examples are provided by way of illustration and should not be construed by way of limitation.

EXAMPLES

Example 1

Effect of PLGA 75:25 Processing

The continuous phase was prepared by weighing 40 g of poly(vinyl alcohol) (PVA) (Mowiol 40-88, Sigma Aldrich, St. Louis, Mo.) and mixing with 4 L of deionized water. The organic phase consisted of 500 mg of PLGA 75:25 (Resomer RG756S) and 267 mg of naltrexone free base (Tecoland Corporation, Irvine, Calif.) dissolved in 1.333 g of dichloromethane (DCM) (Fisher Scientific, Fair Lawn, N.J.) and 623 mg of benzyl alcohol (Fisher Scientific, Fair Lawn, N.J.) in a 20 mL scintillation vial or 500 mg of PLGA 75:25 (Resomer RG756S) and 294 mg of naltrexone free base (Tecoland Corporation, Irvine, Calif.) dissolved in 1.333 g of dichloromethane (DCM) (Fisher Scientific, Fair Lawn, N.J.) and 623 mg of benzyl alcohol (Fisher Scientific, Fair Lawn, N.J.) in a 20 mL scintillation vial. 10 mL of the continuous phase was added to the top of the organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of 1% (w/v) PVA in water and stirred at 4° C. for 8 h. Microparticles were then collected with a 25 µm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then collected on a 25 µm sieve and vacuum dried for 48 h.

Figure 2A:
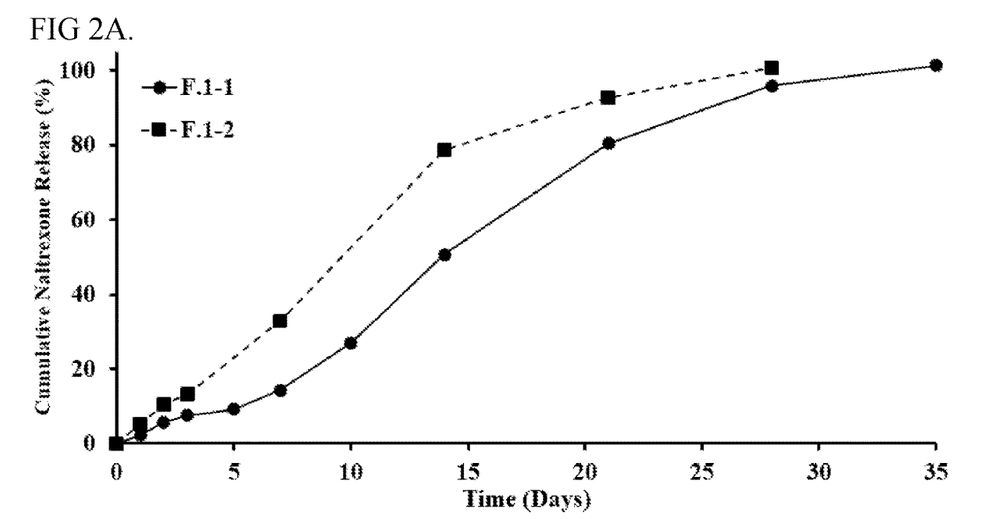
Figure 2B:
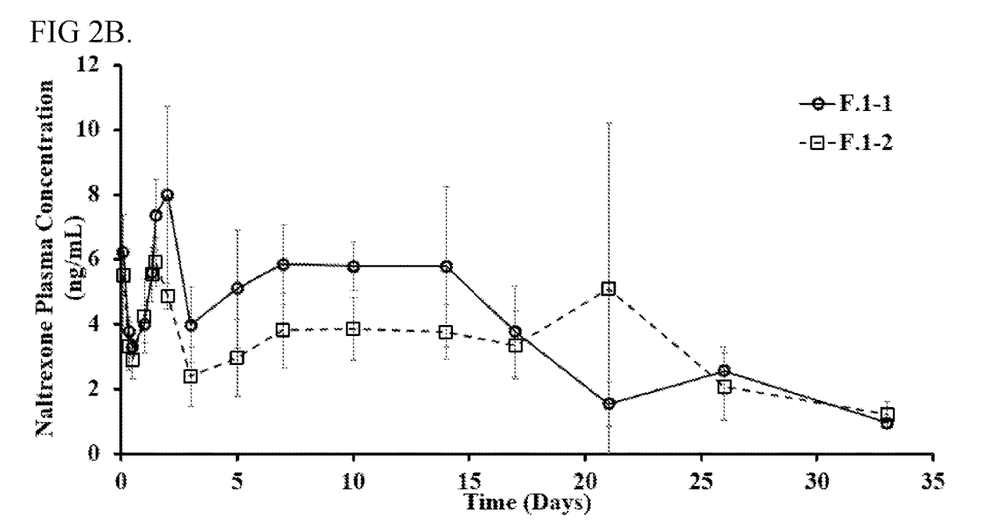
Figure 3:
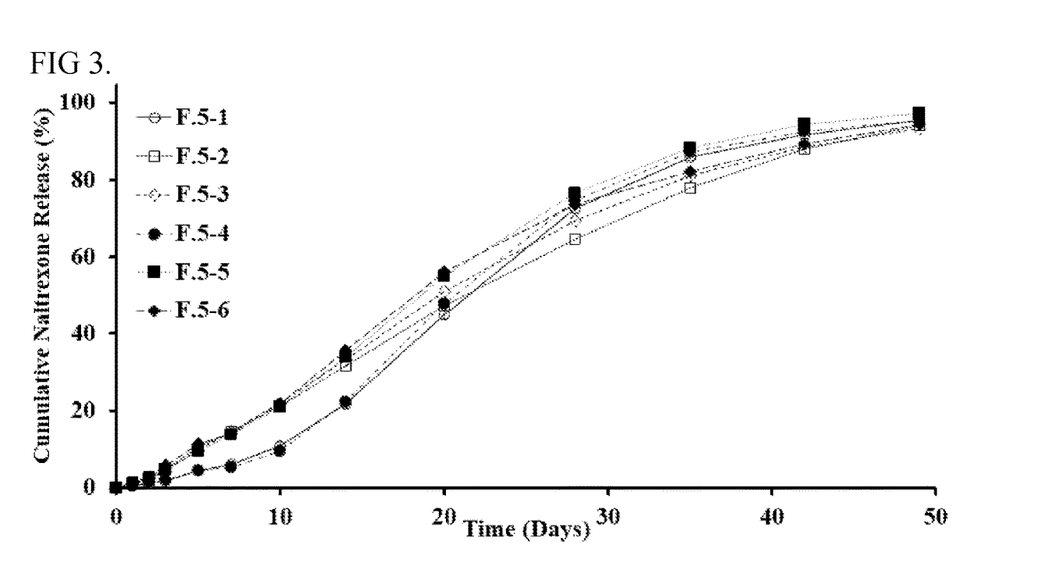
FIG. 3. illustrates the in vitro release of naltrexone from formulations with drug loadings ranging from 37~40% (w/w) from Example 5.
Figure 4A:
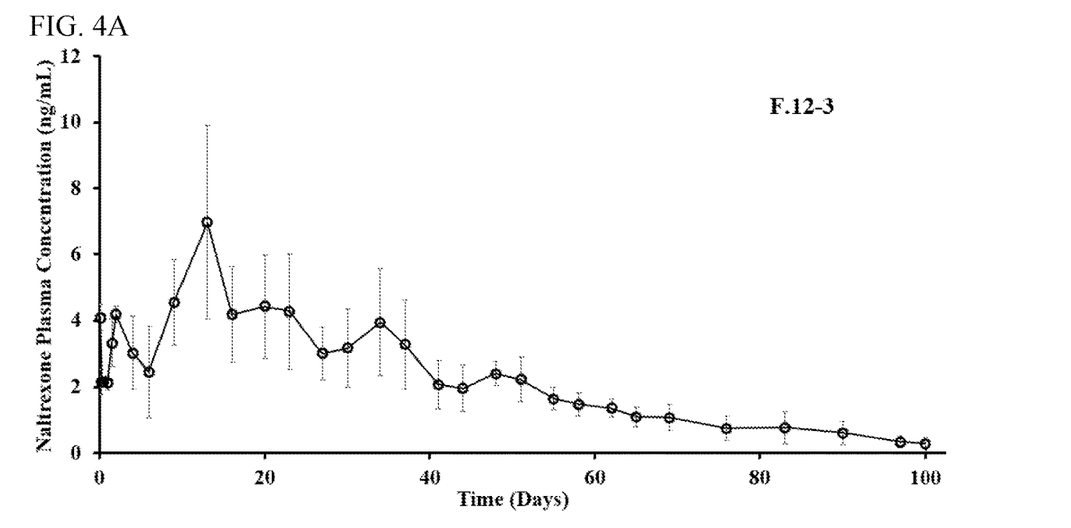
Figure 4B:
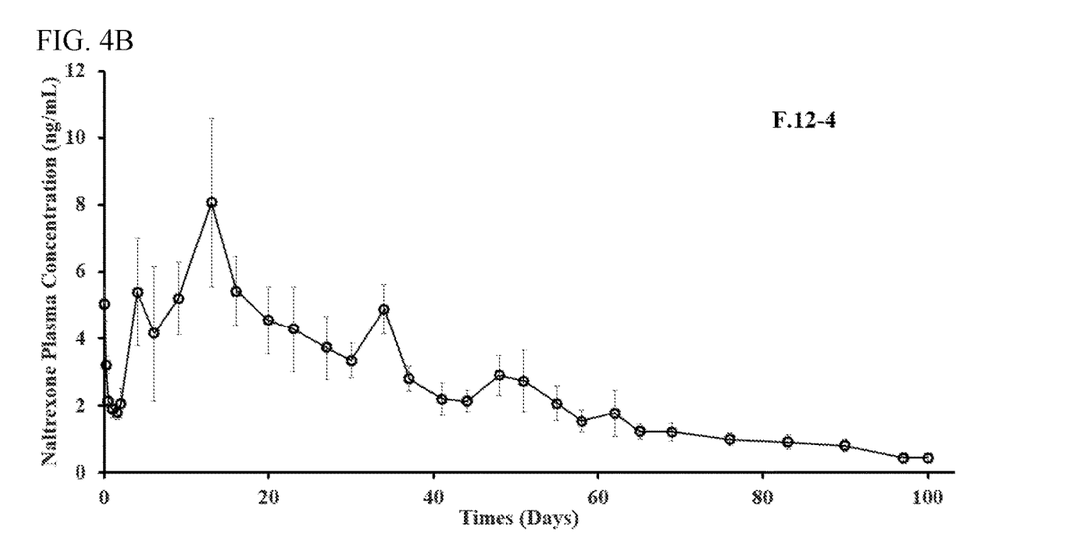
Figure 4C:
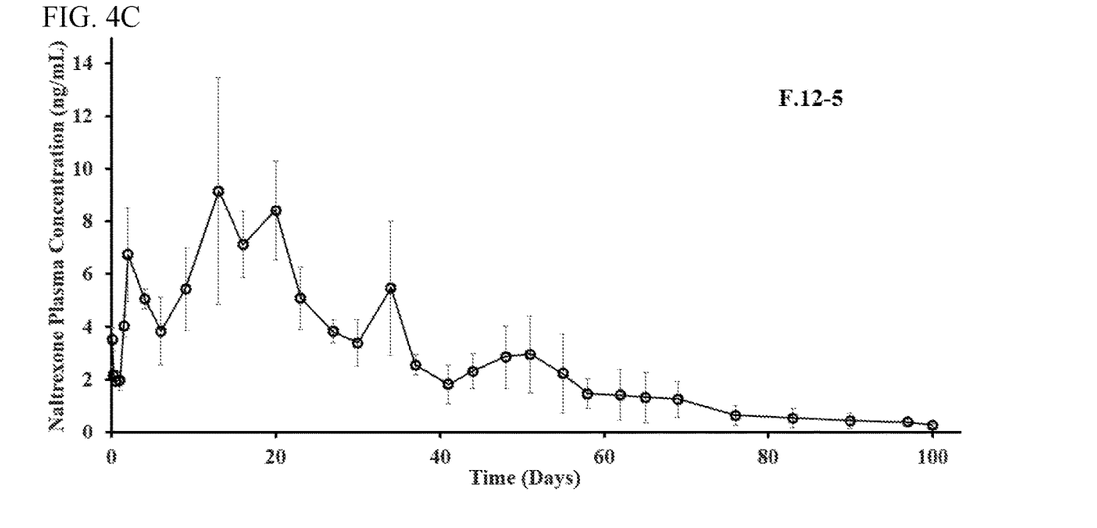
Figure 4D:
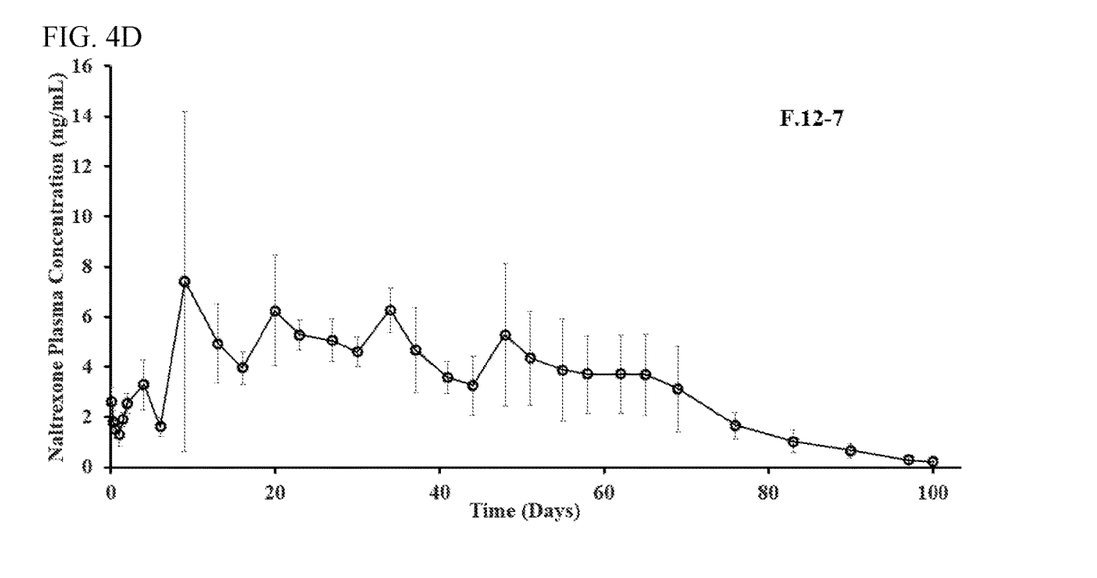

These two formulations were evaluated in pharmacokinetic studies with Sprague-Dawley rats at a dose of 38 mg/kg The resulting drug loading and residual benzyl alcohol content are shown in Table 1. Both formulations provided about 90% encapsulation efficiencies but with release of only approximately 4-5 weeks, with the higher drug loading resulting in faster kinetics. A level A in vitro-in vivo correlation is noted in FIG. 2 for F.1-1, whereas the in vitro test predicts a faster in vivo response than what is observed for F.1-2.

TABLE 1

Formulation summary for Example 1

| Formulation (F) | Starting Naltrexone Weight (mg) | Drug Loading (% w/w) | Residual BA (% w/w) | EE (%) |
|---|---|---|---|---|
| F.1-1 | 267 | 31.2 | 1.31 | 89.7 |
| F.1-2 | 294 | 33.5 | 1.51 | 90.6 |

Drug loading (% w/w) indicates the amount of naltrexone contained in the microparticles, and EE (%) indicates the final amount of remaining naltrexone as compared to the starting naltrexone when preparing the microparticles.

Example 2

Effect of PLGA 75:25 Molecular Weight and Supplier

The continuous phase was prepared by weighing 40 g of poly(vinyl alcohol)(PVA) (Mowiol 40-88, Sigma Aldrich, St. Louis, Mo.) and mixing with 4 L of deionized water. The organic phase consisted of 500 mg of PLGA 75:25 and 267 mg of naltrexone free base (Tecoland Corporation, Irvine, Calif.) dissolved in 1.333 g of dichloromethane (DCM) (Fisher Scientific, Fair Lawn, N.J.) and 623 mg of benzyl alcohol (Fisher Scientific, Fair Lawn, N.J.) in a 20 mL scintillation vial. 10 mL of the continuous phase was added to the top of the organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of deionized water and stirred at 4° C. for 8 h. Microparticles were then collected with a 25 µm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then collected on a 25 µm sieve and vacuum dried for 48 h.

The resulting drug loading and residual benzyl alcohol content are shown in Table 2.

Resomer RG 750 and 756 resulted in similar drug loadings and release profiles, likely due to the similar inherent viscosity, with RG 750 having a wider range. Resomer RG 755 and Lactel B6007-1, with nearly similar inherent viscosity specifications, also resulted in similar drug loadings and release profiles. While resulting in similar drug loadings as the other PLGAs tested, Lactel B6007-2 resulted in a release profile with much faster kinetics. Formulations F.2-1 to F.2-5 provided drug release profiles about 30-35 days.

TABLE 2

Formulation summary for formulations made with 75:25 PLGA

| Formulation (F) | PLGA | Inherent Viscosity (dL/g) | Drug Loading (% w/w) | Residual BA (% w/w) | EE (%) |
|---|---|---|---|---|---|
| F.2-1 | Resomer RG 750 | 0.8-1.2 | 29.2 | 2.86 | 83.8 |
| F.2-2 | Resomer RG 755 | 0.5-0.7 | 28.9 | 1.73 | 83.0 |
| F.2-3 | Resomer RG 756 | 0.71-1.0 | 29.6 | 2.73 | 85.0 |
| F.2-4 | Lactel B6007-1 | 0.55-0.75 | 29.3 | 1.95 | 84.2 |
| F.2-5 | Lactel B6007-2 | 0.8-1.2 | 29.6 | 1.70 | 85.0 |

Example 3

Preparation of Naltrexone Microparticles: Formulation 3

The continuous phase was prepared by weighing 40 g of poly(vinyl alcohol) (PVA) (Mowiol 40-88, Sigma Aldrich, St. Louis, Mo.) and mixing with 4 L of deionized water. The organic phase consisted of 500 mg of PLGA 85:15 (Resomer RG 858S Evonik Cyro, Parsippany, N.J.) and 294 mg of naltrexone free base (Tecoland Corporation, Irvine, Calif.) dissolved in 2.0 g of dichloromethane (DCM) (Fisher Scientific, Fair Lawn, N.J.) and 467 mg of benzyl alcohol (Fisher Scientific, Fair Lawn, N.J.) in a 20 mL scintillation vial. The continuous phase was further mixed with DCM, and 10 mL of the continuous phase with 1.8% (w/v) DCM was added to the top of the organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of the water with 0.5% w/v DCM and stirred at 4° C. for 8 h. Microparticles were collected with a 25 µm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then collected on a 25 µm sieve and vacuum dried for 48 h.

The resulting drug loadings was 28.1% (75.9% EE) and residual benzyl alcohol was 0.55%. The in vitro drug release profile resulted in near zero order release kinetics for approximately 50 days.

Example 4

Preparation of Naltrexone Microparticles: Formulation 4

The continuous phase was prepared by weighing 40 g of PVA and mixing with 4 L of deionized water. The organic phase consisted of 500 mg of PLGA 85:15 (Resomer RG 858S) and 294 mg of naltrexone free base (Tecoland Corporation, Irvine, Calif.) dissolved in 2.0 g of DCM and 623 mg of benzyl alcohol in a 20 mL scintillation vial. The continuous phase was further mixed with DCM, and 10 mL of the continuous phase with 1.8% (w/v) DCM was added to the top of organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of water with 0.66% (w/v) DCM at 4° C. Microparticles were then allowed to stir for 8 h and then collected with 23 µm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then passed through a 125 µm sieve, collected on a 23 µm sieve, and vacuum dried for 48 h.

The resulting drug loading was 21.7% (58.6% EE) and residual benzyl alcohol was 0.83%. A greater amount (0.66% (w/v) of DCM in the extraction phase and higher starting benzyl alcohol contents in the organic phase greatly decreases the drug loading of the formulation. The in vitro drug release profile resulted in near zero order release kinetics for approximately 60 days.

Example 5

Preparation of Naltrexone Microparticles: Effect of Solvent in Emulsification Media The continuous phase was prepared by weighing 40 g of PVA and mixing with 4 L of deionized water. The organic phase consisted of 1.0 g of PLGA 85:15 (Resomer RG 858S) and 818 mg of naltrexone free base (SpecGx, LLC) dissolved in 4.0 g of DCM and 1.908 g of benzyl alcohol in a 20 mL scintillation vial or 1.0 g of PLGA 85:15 (Resomer RG 858S) and 818 mg of naltrexone free base (SpecGx, LLC) dissolved in 4.0 g of DCM and 1.04 g of benzyl alcohol in a 20 mL scintillation vial. 15 mL of the continuous phase or the continuous phase further mixed with DCM or benzyl alcohol (BA) (described in Table 3) was added to the top of the organic phase and homogenized at 7,000 RPM for 60 sec with an IKA T25 homogenizer with S25N-10G generator (IKA Works, Inc. Wilmington, N.C.). The mixture was then transferred into 760 mL of an extraction phase (described in Table 3) and stirred at 4° C. for 4 h. Microparticles were then collected with a 25 µm sieve. The product retained by the sieve was dewatered for 15 min at 22° C. and vacuum dried for about 16 h. The microparticles were then suspended and washed in 400 mL of a 25% (v/v) ethanol solution for 8 h at 22° C. to remove the emulsifying agent (PVA) and any residual solvents from the microparticles. The washed microparticles were then passed through a 125 µm sieve and collected on a 23 µm sieve and vacuum dried for 48 h.

The resulting drug loading and residual benzyl alcohol content can be found in Table 3. An increase in residual benzyl alcohol is seen with a greater starting amount of benzyl alcohol. Encapsulation efficiencies of 80~90% can be obtained. Dichloromethane in the extraction media results in the lowest residual benzyl alcohol contents for this example, although naltrexone is also lost in this process. The drug release curves do not appear to show a difference in release between 3.3% BA (benzyl alcohol) in 1% PVA vs 1% PVA alone. The 1.8% DCM in 1% PVA shows a slightly lower release rate initially, potentially due to the lower drug load.

TABLE 3

Effects of the continuous phase and extraction phase compositions on the resultant drug loading, residual benzyl alcohol (BA), and encapsulation efficiency (EE).

| Formulation (F) | Continuous Phase (w/v)/Extraction Phase (w/v) | Starting BA (g) | Drug Loading (% w/w) | Residual BA (% w/w) | EE (%) |
|---|---|---|---|---|---|
| F.5-1 | 1.8% DCM in 1% PVA in water/ 0.5% DCM in water | 1.908 | 37.0 | 1.44 | 82.2 |
| F.5-2 | 3.3% BA in 1% PVA in water/ H₂O | 1.908 | 39.5 | 2.43 | 87.8 |
| F.5-3 | 1% PVA in water/ H₂O | 1.908 | 39.8 | 2.26 | 88.5 |
| F.5-4 | 1.8% DCM in 1% PVA in water/ 0.5% DCM in water | 1.04 | 37.8 | 0.96 | 84.0 |
| F.5-5 | 3.3% BA in 1% PVA in water/ H₂O | 1.04 | 39.4 | 1.92 | 87.6 |
| F.5-6 | 1% PVA in water/ H₂O | 1.04 | 39.8 | 1.02 | 88.5 |

Example 6

Preparation of Naltrexone Microparticles: Effect of Oil/Water Ratio

The continuous phase was prepared by weighing 40 g of PVA and mixing with 4 L of deionized water. The organic phase consisted of 0.630 g of PLGA 85:15 (Resomer RG 858S) and 370 mg of naltrexone free base (SpecGx, LLC) dissolved in 3.15 g of ethyl acetate (Fisher Scientific, Fair Lawn, N.J.) and 1.17 g of benzyl alcohol in a 20 mL scintillation vial. The continuous phase was further mixed with ethyl acetate, and 20 mL of the continuous phase with 6.525% (w/v) ethyl acetate was emulsified with the organic phase at 4,000 or 7,000 RPM for 30 sec with an IKA T25 homogenizer with S25N-10G generator (IKA Works, Inc. Wilmington, N.C.). The mixture was then transferred into an extraction phase, which is 250 mL of 2.5% (w/v) ethyl acetate in water and stirred at 4° C. for 2 or 4 h. The microparticles were then collected with a 10 μm sieve and dried at 4° C. under vacuum for about 16 h. Microparticles were then suspended and washed in 150 mL of a 25% (v/v) ethanol solution for 8 h at 22° C. to remove the emulsifying agent (PVA) and any residual solvents from the microparticles. The washed microparticles were then passed through a 150 μm sieve and collected on a 10 μm sieve and vacuum dried for 48 h.

The resulting drug loading and residual benzyl alcohol content can be found in Table 4.

The encapsulation efficiencies appear to be lower than formulations prepared under similar conditions with dichloromethane. Minimal differences are observed in the in vitro release profiles of the three formulations, with all formulations lasting slightly longer than approximately 55 days.

TABLE 4

Effects of O/W ratio, homogenization speed, and solvent extraction time on the resultant drug loading, residual benzyl alcohol (BA), and encapsulation efficiency (EE).

| Formulation (F) | O/W ratio (v/v) | Homogenization Speed (RPM) | Solvent Extraction Time (hr) | Drug Loading (% w/w) | Residual BA (% w/w) | EE (%) |
|---|---|---|---|---|---|---|
| F.6-1 | 1/2.82 | 4,000 | 4 | 27.5 | 0.72 | 74.3 |
| F.6-2 | 1/4.35 | 4,000 | 2 | 25.0 | 0.43 | 67.6 |
| F.6-3 | 1/4.35 | 7,000 | 4 | 23.2 | 0.17 | 62.7 |

Example 7

Determination of PLGA Molecular Weight with a Gel-Permeation Chromatography Quaternary Detector Samples of Resomer RG 858S and Lactel B6006-2P were dissolved in acetone to a concentration of approximately 2.5 mg/mL, filtered through a 0.22 μm PTFE filter, and collected into an HPLC auto-sampler vial for injection. The samples were analyzed using GPC-4D. The GPC-4D system consisted of an Agilent 1260 Infinity II HPLC connected to Dawn Heleos II (MALLS) coupled to Dynapro Nanostar DLS via optical cable, Optilab T-rEX (RI detector) and Viscostar III viscometer operated by Astra 7 software. GPC analysis was performed by injecting 50.0 μl of the polymer solution. Separation was performed with a linear gradient column (Tosoh Bioscience LLC, TSKgel GMHHR-L, 7.8 mm×30 cm) at 0.6 ml/min flow of acetone with a 60-minute run time. The molecular weights of the polymer samples are shown in Table 5.

Example 8

Preparation of Naltrexone Microparticles: Effect of 85:15 Molecular Weight and Extraction Time The continuous phase was prepared by weighing 40 g of PVA and mixing with 4 L of deionized water. The organic phase consisted of 500 mg of PLGA 85:15 (Resomer RG 858S (IV 1.3-1.7 dL/g, Lot Number D161000568, Evonik Cyro, Parsippany, N.J.) or Lactel B6006-2P (IV 0.76-0.85 dL/g, Lot Number A17-068, Durect, Cupertino, Calif.)) and 267 mg of naltrexone free base (SpecGx, LLC) dissolved in 2.0 g of DCM and 623 mg of benzyl alcohol in a 20 mL scintillation vial. The continuous phase was further mixed with DCM, and 10 mL of the continuous phase containing 1.8% (w/v) DCM was added to the organic phase and emulsified at 7,000 RPM for 60 sec with an IKA T25 homogenizer with S25N-10G generator (IKA Works, Inc. Wilmington, N.C.). The mixture was then transferred into an extraction phase (380 mL of 0.5% (w/v) dichloromethane in water) and stirred at 4° C. for 2, 4, or 7 h. The microparticles were then collected with a 25 μm sieve and dried at 4° C. under vacuum for about 16 h. Microparticles were then suspended and washed in 200 mL of a 25% (v/v) ethanol solution for 8 h at 22° C. to remove PVA and any residual solvents from the microparticles. The washed microparticles were then passed through a 125 μm sieve and collected on a 25 μm sieve and vacuum dried for 48 h.

The resultant drug loadings, residual benzyl alcohol content, and encapsulation efficiency can be found in Table 6. Minimal effects of extraction time were noted between the two types of PLGA and their respective drug loading. The residual benzyl alcohol appears to be slightly higher for the Lactel batches vs the Resomer batches. The extraction time does not appear to have an effect on the release rate, whereas differences in the release profile between the two polymers is evident. The Resomer batches appear to have a shorter lag phase vs the Lactel batches, resulting in a more steady-state release over 60 days in vitro compared to the Lactel batches.

TABLE 5

$M_n$ (number average molecular weight), $M_w$ (weight average molecular weight), $M_z$ (higher average molecular weight), $M_{avg}$ (average molecular weight), and polydispersity

| Excipient (E) | Polymer | Lot Number | $M_n$ (kDa) | $M_w$ (kDa) | $M_z$ (kDa) | $M_{avg}$ (kDa) | Polydispersity ($M_w/M_n$) |
|---|---|---|---|---|---|---|---|
| E.7-1 | Resomer RG 858S | D161000568 | 120.15 | 141.07 | 171.75 | 121.95 | 1.17 |
| E.7-2 | Lactel B6006-2P | A17-028 | 66.01 | 78.19 | 94.40 | 65.41 | 1.19 |

TABLE 6

Effects of PLGA and extraction time on the resultant drug loading, residual benzyl alcohol (BA), and encapsulation efficiency (EE).

| Formulation (F) | PLGA | Extraction Time (hr) | Drug Loading (% w/w) | Residual BA (% w/w) | EE (%) |
|---|---|---|---|---|---|
| F.8-1 | Resomer RG | 2 | 28.0 | 0.88 | 80.5 |
| F.8-2 | 858S | 4 | 27.7 | 0.88 | 79.6 |
| F.8-3 |  | 7 | 28.6 | 0.89 | 82.2 |
| F.8-4 | Lactel B6006-2 | 2 | 27.5 | 1.16 | 79.0 |
| F.8-5 |  | 4 | 28.1 | 1.06 | 80.7 |
| F.8-6 |  | 7 | 28.5 | 1.12 | 81.9 |

Example 9

Preparation of Naltrexone Microparticles: Effect of No Ethanol Wash Vs 25% Ethanol Wash The continuous phase was prepared by weighing 40 g of PVA and mixing with 4 L of deionized water. The organic phase consisted of 500 mg of PLGA 85:15 (Resomer RG 858S) and 267 mg of naltrexone free base (SpecGx, LLC) dissolved in 2.0 g of DCM and 623 mg of benzyl alcohol in a 20 mL scintillation vial. The continuous phase was further mixed with DCM, and 10 mL of the continuous phase containing 1.8% (w/v) DCM was added to the organic phase and emulsified at 7,000 RPM for 60 sec with an IKA T25 homogenizer with S25N-10G generator (IKA Works, Inc. Wilmington, N.C.). The mixture was then transferred into an extraction phase (380 mL of 0.5% (w/v) DCM in water) and stirred at 4° C. for 2 h. Microparticles were then collected with a 25 µm sieve and dried at 4° C. under vacuum for about 16 h. The microparticles were then suspended and washed in 200 mL of a 25% (v/v) ethanol solution for 8 h at 22° C. to remove PVA and any residual solvents from the microparticles or passed through a 125 µm sieve and vacuum dried for 48 h. The washed microparticles were then passed through a 125 µm sieve and collected on a 25 µm sieve and vacuum dried for 48 h.

The resultant drug loadings, residual benzyl alcohol content, and encapsulation efficiency can be found in Table 7. The ethanol wash resulted in microparticles that had a lower residual benzyl alcohol content, and higher drug load—likely due to the benzyl alcohol extraction. The initial 10 days of release is similar between the washed and unwashed particles, but the rate post-10 days is faster for the unwashed particles vs. washed particles.

TABLE 7

Effects of PLGA and extraction time on the resultant drug loading, residual benzyl alcohol (BA), and encapsulation efficiency (EE).

| Formulation (F) | Process | Drug Loading (% w/w) | Residual BA (% w/w) | EE (%) |
|---|---|---|---|---|
| F.9-1 | No Ethanol Wash | 27.9 | 1.71 | 80.2 |
| F.9-2 | 25% Ethanol Wash | 28.3 | 0.86 | 81.3 |

Example 10

Preparation of Naltrexone Microparticles: Effect of Ethanol Wash Concentration

The continuous phase was prepared by weighing 40 g of PVA and mixing with 4 L of deionized water. The organic phase consisted of 500 mg of PLGA 85:15 (Resomer RG 858S) and 305 mg of naltrexone free base (SpecGx, LLC) dissolved in 2.0 g of DCM and 467 mg of benzyl alcohol in a 20 mL scintillation vial. The continuous phase was further mixed with DCM, and 10 mL of the continuous phase with 1.8% (w/v) DCM was added to the organic phase and emulsified at 7,000 RPM for 60 sec with an IKA T25 homogenizer with S25N-10G generator (IKA Works, Inc. Wilmington, N.C.). The mixture was then transferred into an extraction phase (380 mL with 0.33% (w/v) DCM in water) and stirred at 4° C. for 8 h. The microparticles were then collected with a 25 µm sieve and dried at 4° C. under vacuum for about 16 h. Microparticles were then suspended and washed in 200 mL of a 6.25, 12.5, 25, or 50% (v/v) ethanol solution for 8 h at 22° C. to remove PVA and any residual solvents from the microparticles. The washed microparticles were then passed through a 125 µm sieve and collected on a 25 µm sieve and vacuum dried for 48 h.

The resulting drug loadings, residual benzyl alcohol content, and encapsulation efficiency can be found in Table 8. The drug loadings for a 6.25, 12.5, and 25% (v/v) did not result in any significant differences or trend. The residual benzyl alcohol content decreases with an increase in ethanol wash concentration for this condition. At 50% (v/v) a significant amount of naltrexone is lost during the wash and naltrexone release was much faster relative to the 6.25, 12.5, and 25% condition.

TABLE 8

Effects of ethanol wash concentration on the resultant drug loading, residual benzyl alcohol (BA), and encapsulation efficiency (EE).

| Formulation (F) | Ethanol Wash Concentration (% v/v) | Drug Loading (% w/w) | Residual BA (% w/w) | EE (%) |
|---|---|---|---|---|
| F.10-1 | 6.25 | 29.5 | 0.77 | 77.8 |
| F.10-2 | 12.5 | 29.2 | 0.67 | 77.0 |
| F.10-3 | 25 | 29.4 | 0.41 | 77.5 |
| F.10-4 | 50 | 23.9 | 0.00 | 63.1 |

Example 11

Preparation of Naltrexone Microparticles: Effect of Ethanol Wash Temperature

The continuous phase was prepared by weighing 40 g of PVA and mixing with 4 L of deionized water. The organic phase consisted of 500 mg of PLGA 85:15 (Resomer RG 858S) and 294 mg of naltrexone free base (SpecGx, LLC) dissolved in 2.0 g of DCM and 467 mg of benzyl alcohol (Fisher Scientific, Fair Lawn, N.J.) in a 20 mL scintillation vial. The continuous phase was further mixed with dichloromethane, and 10 mL of the continuous phase with 1.8% (w/v) dichloromethane was added to the organic phase and emulsified at 7,000 RPM for 60 sec with an IKA T25 homogenizer with S25N-10G generator (IKA Works, Inc. Wilmington, N.C.). The mixture was then transferred into an extraction phase (380 mL of 1% (w/v) PVA in water) and stirred at 4° C. for 8 h. Microparticles were then collected with a 25 µm sieve and dried at 4° C. under vacuum for about 16 h. The microparticles were then suspended and washed in 200 mL of a 25% (v/v) ethanol solution for 8 h at 4° C. or 22° C. to remove the emulsifying agent (PVA) and any residual solvents from the microparticles. The washed microparticles were then passed through a 125 µm sieve and collected on a 25 µm sieve and vacuum dried for 48 h. The resulting drug loadings, residual benzyl alcohol content, and encapsulation efficiency can be found in Table 9.

The ethanol wash at 22° C. resulted in microparticles that had a lower residual benzyl alcohol content, and higher drug load—likely due to the benzyl alcohol extraction. The release of naltrexone from microparticles washed at 22° C. resulted in a quicker release rate until 10 days. The release of naltrexone from microparticles at 4° C. resulted in a quicker release rate after the initial 10 days and only lasted approximately 35 days in vitro, whereas the 22° C. washed particles provided naltrexone release for approximately 50 days.

TABLE 9

Effects of ethanol wash concentration on the resultant drug loading, residual benzyl alcohol (BA), and encapsulation efficiency (EE).

| Formulation (F) | Ethanol Wash Temperature (° C.) | Drug Loading (% w/w) | Residual BA (% w/w) | EE (%) |
|---|---|---|---|---|
| F.11-1 | 4 | 32.1 | 1.61 | 86.6 |
| F.11-2 | 22 | 32.9 | 0.76 | 88.9 |

Example 12

In Vivo Response of Formulations

Seven formulations with naltrexone (free base) loadings from ~20% to ~40% were evaluated in pharmacokinetic studies with Sprague-Dawley rats. Among the seven formulations, each of F.12-1, F.12-2, F.12-4, and F.12-6 was prepared in the same manner as F.3-5, F.4-1, F.8-6, and F.5-4, whereas F.12-3, F.12-5, and F.12-7 were prepared as described below.

F.12-3

The continuous phase was prepared by weighing 40 g of poly(vinyl alcohol) (PVA) (Mowiol 40-88, Sigma Aldrich, St. Louis, Mo.) and mixing with 4 L of deionized water. The organic phase consisted of 500 mg of PLGA 85:15 (Resomer RG858S) and 294 mg of naltrexone free base (Tecoland Corporation, Irvine, Calif.) dissolved in 2.0 g of dichloromethane (DCM) (Fisher Scientific, Fair Lawn, N.J.) and 467 mg of benzyl alcohol (Fisher Scientific, Fair Lawn, N.J. 10 mL of the continuous phase was added to the top of the organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of 1% (w/v) PVA in water and stirred at 4° C. for 8 h. Microparticles were then collected with a 25 μm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then collected on a 25 μm sieve and vacuum dried for 48 h.

F.12-5

The continuous phase was prepared by weighing 40 g of poly(vinyl alcohol) (PVA) (Mowiol 40-88, Sigma Aldrich, St. Louis, Mo.) and mixing with 4 L of deionized water. The organic phase consisted of 500 mg of PLGA 85:15 (Resomer RG858S) and 409 mg of naltrexone free base (Tecoland Corporation, Irvine, Calif.) dissolved in 2.0 g of dichloromethane (DCM) (Fisher Scientific, Fair Lawn, N.J.) and 623 mg of benzyl alcohol (Fisher Scientific, Fair Lawn, N.J.) in a 20 mL scintillation vial. The continuous phase was further mixed with dichloromethane, and 10 mL of the continuous phase with 1.8% (w/v) DCM was added to the top of the organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of 0.5% (w/v) DCM in water and stirred at 4° C. for 4 h. Microparticles were then collected with a 25 μm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then collected on a 25 μm sieve and vacuum dried for 48 h.

F.12-7

The continuous phase was prepared by weighing 40 g of poly(vinyl alcohol) (PVA) (Mowiol 40-88, Sigma Aldrich, St. Louis, Mo.) and mixing with 4 L of deionized water. The organic phase consisted of 500 mg of PLGA 85:15 (Resomer RG858S) and 267 mg of naltrexone free base (Tecoland Corporation, Irvine, Calif.) dissolved in 2.0 g of dichloromethane (DCM) (Fisher Scientific, Fair Lawn, N.J.) and 623 mg of benzyl alcohol (Fisher Scientific, Fair Lawn, N.J.) in a 20 mL scintillation vial. The continuous phase was further mixed with dichloromethane, and 10 mL of the continuous phase with 1.8% (w/v) DCM was added to the top of the organic phase and homogenized at 7,000 RPM for 60 sec with an IKA T25 homogenizer with S25N-10G generator (IKA Works, Inc. Wilmington, N.C.). The mixture was then transferred into an extraction phase, which is 380 mL of 0.5% (w/v) DCM in water and stirred at 4° C. for 7 h. Microparticles were then collected with a 25 μm sieve. The product retained by the sieve was dewatered for 15 min at 22° C. and vacuum dried for about 16 h. The microparticles were then suspended and washed in 200 mL of a 25% (v/v) ethanol solution for 8 h at 22° C. to remove the emulsifying agent (PVA) and any residual solvents from the microparticles. The washed microparticles were then collected on a 25 μm sieve and vacuum dried for 48 h.

The effect of drug loading, solvent system, and solvent concentration on naltrexone release was evaluated. The lowest drug loading sample (F.12-2), resulted in what appears to be the largest burst release, relative to the formulations steady state release. As the drug load increased from approximately 28% to 38%, higher concentrations from around day 2 to day 20 were observed, but the formulations observed similar steady state plasma concentrations after day 20 of between approximately 1.5 to 4 ng/mL until approximately day 60. The naltrexone concentration of 0.5 ng/mL was maintained for about 100 days.

TABLE 10

| Formulation (F) | PLGA Concentration in DCM or EA (% w/w) | Naltrexone Concentration in BA (% w/w) | Organic Phase Solvent System | Dose Level (mg/kg) | Drug Loading (% w/w) | EE (%) |
|---|---|---|---|---|---|---|
| F.12-1 | 20.0 | 38.6 | DCM/BA | 76 | 28.1 | 80.7 |
| F.12-2 | 20.0 | 32.1 | DCM/BA | 76 | 21.7 | 58.6 |
| F.12-3 | 20.0 | 38.6 | DCM/BA | 50 | 34.2 | 92.4 |
| F.12-4 | 15.0 | 24.0 | EA/BA | 50 | 28.5 | 77.0 |
| F.12-5 | 20.0 | 39.6 | DCM/BA | 50 | 36.1 | 80.2 |
| F.12-6 | 20.0 | 44.0 | DCM/BA | 50 | 37.8 | 84.0 |
| F.12-7 | 20.0 | 30.0 | DCM/BA | 50 | 27.8 | 79.9 |

Drug Loading (% w/w) is based on the microparticle weight.

Test Procedures

In Vitro Release of Naltrexone from Test Formulations

The medium, 20 mL of pH 7.4 phosphate buffered saline with 0.05% Tween 20 (Sigma Aldrich, St. Louis, Mo.) and 0.0625% (w/v) sodium ascorbate (Sigma Aldrich, St. Louis, Mo.) and approximately 5 mg of test article were placed in a stoppered 50 mL Erlenmeyer flask and placed in a 37° C. water bath at 100 RPM. Samples were taken at various time points and replaced with fresh release medium. Naltrexone content in buffer was measured via High Performance Liquid Chromatography (HPLC).

Reversed Phase HPLC for the Quantitation of Naltrexone

The HPLC had the following conditions: Mobile Phase: 65:35 methanol:potassium phosphate buffer, pH 6.6; flow rate: 1.0 ml/min; autosampler temperature:room temperature; column temperature: 30° C.; detection: 210 nm (UV); total run time: 7 min; injection volume: 10 μL; column: Zorbax SB-C18 150×4.6 mm, 5 μm; approximate retention time of naltrexone: 4.8 min.

In Vivo Pharmacokinetic Studies

All rat preclinical studies were conducted in Sprague-Dawley rats. Three to five rats per test formulation were injected subcutaneously in the scruff behind the neck or in the scapular region with a dosage of naltrexone ranging from 50 mg/kg to 100 mg/kg in 1 ml of an aqueous-based vehicle, composed of 0.9% sodium chloride, 0.02% Tween 20, and 0.5% sodium carboxymethylcellulose.

During the course of the study, the animals were observed for overt toxicity and any existing test site abnormalities, including redness, swelling, bleeding, discharge, and bruising at the injection site. In addition, body weights were taken and recorded at administration and at the conclusion of the study.

At selected time points, rats were anesthetized and bled (approximately 250 μL) via the tail or submandibular vein. Blood was collected in labeled potassium ethylenediaminetetraacetic acid tubes. The blood was centrifuged for 10 min at 4,000 rpm at 4° C. The plasma fraction was transferred to labeled 1 mL plastic tubes and stored at −80° C. prior to analysis.

What is claimed is:

1. An injectable microparticle formulation comprising a microparticle including naltrexone and poly(lactide-co-glycolide) with a lactide:glycolide ratio of about 85:15, wherein sustained release of naltrexone is longer than 4 weeks and up to 100 days.

2. The microparticle formulation according to claim 1, wherein sustained release of naltrexone is about 8 weeks to about 12 weeks.

3. The microparticle formulation according to claim 1, wherein the naltrexone is in the form of free base, salt, solvate, cocrystal or combinations thereof.

4. The microparticle formulation according to claim 1, wherein the naltrexone is about 20-40% (w/w) of the microparticle.

5. The microparticle formulation according to claim 1, wherein the poly(lactide-co-glycolide) has a number average molecular weight of 50,000 to 150,000 Daltons.

6. The microparticle formulation according to claim 1, wherein the microparticle is administered in a biocompatible vehicle, including an aqueous-based vehicle, an oil-based vehicle or combination thereof.

7. The microparticle formulation according to claim 6, wherein the aqueous based vehicle comprises a tonicity agent such as sodium chloride, a viscosity enhancing agent such as sodium carboxymethylcellulose, a wetting agent such as polysorbate, or combinations thereof.

8. The microparticle formulation according to claim 6, wherein the oil-based vehicle comprises peanut oil, sesame oil, cottonseed oil, or combinations thereof.

9. The microparticle formulation according to claim 1, wherein the microparticles have particle size in the range of 25 to 125 μm.

10. A method for treating or preventing diseases related to opioid abuse or overdoses, alcohol dependence or pain comprising administering an effective amount of the injectable microparticle formulation according to claim 1 to a subject in need of such a treatment or prevention.

11. A method for preparing the injectable microparticle formulation according to claim 1, the method comprising:
   (a) mixing a first phase comprising polyvinyl alcohol and a first solvent, and a second phase comprising a biodegradable polymer, naltrexone and a second solvent to prepare a mixture; and
   (b) performing an extraction process on the mixture with water or an aqueous solution to obtain microparticles.

12. The method according to claim 11, wherein the first solvent comprises at least one selected from the group consisting of water, dichloromethane benzyl alcohol, and ethyl acetate.

13. The method according to claim 11, wherein the second solvent comprises at least one selected from the group consisting of dichloromethane, benzyl alcohol, and ethyl acetate.

14. The method according to claim 11, the aqueous solution comprises at least one selected from the group consisting of polyvinyl alcohol, dichloromethane, benzyl alcohol, and ethyl acetate.

15. The method according to claim 11, wherein the biodegradable polymer comprises a polylactide, poly(lactide-co-glycolide), or combinations thereof, wherein a lactide:glycolide ratio of the biodegradable polymer is 50:50 to 100:0.

16. The method according to claim 11, wherein the method further comprises (c) performing a further extraction process on the microparticles with an ethanolic aqueous solution after the (b) performing the extraction process.

17. The method according to claim 16, wherein the method further comprises drying the microparticles, wherein the drying is performed after the (b) performing the extraction process, after the (c) performing the further extraction process, or after each of the (b) and (c).

* * * * *

UNITED STATES PATENT AND TRADEMARK OFFICE
CERTIFICATE OF CORRECTION

PATENT NO. : 11,000,479 B2  
APPLICATION NO. : 16/653707  
DATED : May 11, 2021  
INVENTOR(S) : Gwangheum Yoon et al.

Page 1 of 1

It is certified that error appears in the above-identified patent and that said Letters Patent is hereby corrected as shown below:

In the Claims

Column 19, Line 61, In Claim 1:  
Delete "including" and insert -- comprising --, therefor.

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*